(12) United States Patent
Gonnelli

(10) Patent No.: US 8,920,375 B2
(45) Date of Patent: Dec. 30, 2014

(54) GAS PRESSURE ACTUATED MICRONEEDLE ARRAYS, AND SYSTEMS AND METHODS RELATING TO SAME

(75) Inventor: Robert R. Gonnelli, Mahwah, NJ (US)

(73) Assignee: Valeritas, Inc., Bridgewater, NJ (US)

( * ) Notice: Subject to any disclaimer, the term of this patent is extended or adjusted under 35 U.S.C. 154(b) by 0 days.

(21) Appl. No.: 10/252,739

(22) Filed: Sep. 23, 2002

(65) Prior Publication Data

US 2003/0135158 A1 Jul. 17, 2003

Related U.S. Application Data

(60) Provisional application No. 60/323,852, filed on Sep. 21, 2001.

(51) Int. Cl.
*A61M 37/00* (2006.01)
*A61L 31/16* (2006.01)

(52) U.S. Cl.
CPC .......... *A61L 31/16* (2013.01); *A61M 2037/003* (2013.01); *A61L 2300/00* (2013.01); *A61M 37/0015* (2013.01)
USPC .......................................... 604/141; 604/247

(58) Field of Classification Search
USPC .............. 604/93.01, 131, 133, 264, 246, 247, 604/140–141, 145–146, 245, 20–22
See application file for complete search history.

(56) References Cited

U.S. PATENT DOCUMENTS

| 2,893,392 A | 7/1959 | Wagner et al. |
| 3,034,507 A | 5/1962 | McConnell et al. |
| 3,086,530 A | 4/1963 | Groom |
| 3,123,212 A | 3/1964 | Taylor et al. |
| 3,136,314 A | 6/1964 | Kravitz |
| RE25,637 E | 9/1964 | Kravitz et al. |
| 3,221,739 A | 12/1965 | Rosenthal |
| 3,221,740 A | 12/1965 | Rosenthal |
| 3,556,080 A | 1/1971 | Hein |
| 3,596,660 A | 8/1971 | Melone |
| 3,675,766 A | 7/1972 | Rosenthal |
| 3,814,097 A * | 6/1974 | Ganderton et al. ........... 604/304 |
| 3,918,449 A | 11/1975 | Pistor |
| 3,964,482 A * | 6/1976 | Gerstel et al. .............. 604/890.1 |
| 4,109,655 A | 8/1978 | Chacornac |
| 4,159,659 A | 7/1979 | Nightingale |

(Continued)

FOREIGN PATENT DOCUMENTS

| EP | 0 497 620 B1 | 5/1992 |
| EP | 0 652 600 B1 | 5/1995 |

(Continued)

OTHER PUBLICATIONS

US 2003/0014014 A1, Jan. 16, 2003, Nitzan.*

(Continued)

*Primary Examiner* — Kevin C Sirmons
*Assistant Examiner* — Phillip Gray
(74) *Attorney, Agent, or Firm* — Lisa M. Warren, Esq.; Morse, Barnes-Brown & Pendleton, P.C.

(57) ABSTRACT

The microneedle devices disclosed herein in some embodiments include a substrate; one or more microneedles; a reservoir for delivery of drugs; a gas source, and, optionally, pump(s), sensor(s), and/or microprocessor(s) to control the interaction of the foregoing.

22 Claims, 2 Drawing Sheets

(56) References Cited

U.S. PATENT DOCUMENTS

| | | | |
|---|---|---|---|
| 4,222,392 A | 9/1980 | Brennan | |
| 4,320,758 A | 3/1982 | Eckenhoff et al. | |
| 4,664,651 A | 5/1987 | Weinsbenker et al. | |
| 4,671,288 A | 6/1987 | Gough | |
| 4,703,761 A | 11/1987 | Rathbone et al. | |
| 4,771,660 A | 9/1988 | Yacowitz | |
| 4,775,361 A | 10/1988 | Jacques et al. | |
| 4,798,582 A | 1/1989 | Sarath et al. | |
| 4,921,475 A | 5/1990 | Sibalis | |
| 4,969,468 A | 11/1990 | Byers et al. | |
| 5,035,711 A | 7/1991 | Aoki et al. | |
| 5,054,339 A | 10/1991 | Yacowitz | |
| 5,138,220 A | 8/1992 | Kirkpatrick | |
| 5,147,355 A | 9/1992 | Friedman et al. | |
| 5,250,023 A | 10/1993 | Lee et al. | |
| 5,279,544 A * | 1/1994 | Gross et al. | 604/20 |
| 5,279,552 A | 1/1994 | Magnet | |
| 5,335,670 A | 8/1994 | Fishman | |
| 5,364,374 A | 11/1994 | Morrison et al. | |
| 5,383,512 A | 1/1995 | Jarvis | |
| 5,401,242 A | 3/1995 | Yacowitz | |
| 5,457,041 A | 10/1995 | Ginaven et al. | |
| 5,527,288 A | 6/1996 | Gross et al. | |
| 5,582,184 A | 12/1996 | Erickson et al. | |
| 5,591,139 A | 1/1997 | Lin et al. | |
| 5,599,302 A | 2/1997 | Lilley et al. | |
| 5,605,662 A | 2/1997 | Heller et al. | |
| 5,611,806 A | 3/1997 | Jang | |
| 5,611,809 A | 3/1997 | Marshall et al. | |
| 5,611,942 A | 3/1997 | Mitsui et al. | |
| 5,618,295 A | 4/1997 | Min | |
| 5,632,957 A | 5/1997 | Heller et al. | |
| 5,658,515 A | 8/1997 | Lee et al. | |
| 5,697,901 A | 12/1997 | Eriksson | |
| 5,758,505 A | 6/1998 | Dobak et al. | |
| 5,801,057 A | 9/1998 | Smart et al. | |
| 5,807,375 A | 9/1998 | Gross et al. | |
| 5,843,114 A | 12/1998 | Jang | |
| 5,848,991 A | 12/1998 | Gross et al. | |
| 5,852,495 A | 12/1998 | Parce | |
| 5,855,801 A | 1/1999 | Lin et al. | |
| 5,858,188 A | 1/1999 | Soane et al. | |
| 5,865,786 A | 2/1999 | Sibalis et al. | |
| 5,865,796 A | 2/1999 | McCabe | |
| 5,876,675 A | 3/1999 | Kennedy | |
| 5,879,326 A | 3/1999 | Godshall et al. | |
| 5,883,211 A | 3/1999 | Sassi et al. | |
| 5,885,211 A | 3/1999 | Eppstein et al. | |
| 5,899,880 A | 5/1999 | Bellhouse et al. | |
| 5,911,223 A | 6/1999 | Weaver et al. | |
| 5,919,159 A | 7/1999 | Lilley et al. | |
| 6,050,988 A | 4/2000 | Zuck | |
| 6,080,116 A | 6/2000 | Erickson et al. | |
| 6,132,755 A | 10/2000 | Eicher et al. | |
| 6,312,612 B1 | 11/2001 | Sherman et al. | |
| 6,334,856 B1 | 1/2002 | Allen et al. | |
| 6,558,361 B1 * | 5/2003 | Yeshurun | 604/272 |
| 6,565,532 B1 * | 5/2003 | Yuzhakov et al. | 604/142 |
| 6,692,456 B1 * | 2/2004 | Eppstein et al. | 604/22 |
| 6,743,211 B1 * | 6/2004 | Prausnitz et al. | 604/239 |
| 6,939,324 B2 * | 9/2005 | Gonnelli et al. | 604/142 |
| 2001/0053891 A1 | 12/2001 | Ackley | |

FOREIGN PATENT DOCUMENTS

| | | |
|---|---|---|
| JP | 07132119 A | 5/1995 |
| JP | 7196314 A | 8/1995 |
| WO | WO 93/17754 A1 | 9/1993 |
| WO | WO 96/37256 A1 | 11/1996 |
| WO | WO 96/40365 A1 | 12/1996 |
| WO | WO 96/41236 A1 | 12/1996 |
| WO | WO 97/07734 A1 | 3/1997 |
| WO | WO 98/00193 A1 | 1/1998 |
| WO | WO 98/00194 A2 | 1/1998 |
| WO | WO 98/28037 A1 | 7/1998 |
| WO | WO 00/48669 A1 | 8/2000 |
| WO | WO 00/74763 A2 | 12/2000 |

OTHER PUBLICATIONS

101 Uses for Tiny Tubules. Science 247 (Mar. 23, 1990).

Abrams, S.B. Versatile biosensor is compact and cheap. Biophotonics International 32-34 (Jan./Feb. 1998).

Amsden, B.G. and Goosen, M.F.A. Transdermal Delivery of Peptide and Protein Drugs: an Overview. AIChE J. 41, 1972-1977 (Aug. 1995).

Brumlik, C.J. and Martin, C.R. Template Synthesis of Metal Microtubules. J. Am. Chem. Soc. 113, 3174-3175 (1991).

Chun, K. et al. Fabrication of Array of Hollow Microcapillaries Used for Injection of Genetic Materials into Animal/Plant Cells. Jpn. J. Appl. Phys. 38, 279-281 (1999).

Clarke, M.S.F. and McNeil, P.L. Syringe loading introduces macromolecules into living mammalian cell cytosol. J. Cell. Sci. 102, 533-541 (1992).

Despont, M. et al. High-Aspect-Ratio, Ultrathick, Negative-Tone Near-UV Photoresist for Mems Applications. IEEE 0-7803-3744-1/97 (1997).

Edell, D.J. et al. Factors Influencing the Biocompatibility of Insertable Silicon Microshafts in Cerebral Cortex. IEEE Transactions on Biomedical Engineering 39, 635-643 (1992).

Eleventh Annual International Workshop on Micro Electro Mechanical Systems, Heidelberg, Germany (Jan. 25-29, 1998). IEEE Catalog No. 98CH36176.

Frazier, A.B. et al. Two Dimensional Metallic Microelectrode Arrays for Extracellular Stimulation and Recording of Neurons. IEEE 0-7803-0957 pp. 195-200 (Feb. 1993).

Frazier, A.B. and Allen, M.G. Metallic Microstructures Fabricated Using Photosensitive Polymide Electroplating Molds. J. Microelectromechanical Systems 2, 87-94 (Jun. 1993).

Haga et al. Transdermal Iontophoretic delivery of insulin using a photoetched microdevice. J. Controlled Release 43, 139-149 (1997).

Hashmi, S. et al. Genetic Transformation of Nematodes Using Arrays of Micromechanical Piercing Structures. BioTechniques 19, 766-770 (Nov. 1995).

Henry, S. et al. Micromachined Needles: A Novel Approach to Transdermal Drug Delivery. J. Pharm. Sci. 87, 922-925 (Aug. 1998).

Henry et al. Microfabricated Microneedles: A Novel Method to Increase Transdermal Drug Delivery. J. Pharm. Sci. 87, 922-925 (1998).

Hoffert, S.P. Transcutaneous Methods Get Under the Skin. The Scientist 12, No. 16 (Aug. 17, 1998).

Infiltrator Intramural Drug Delivery: A New Generation of Drug Delivery Catheters from InterVentional Technologies, Inc., San Diego, CA (1997).

Jaeger, R.C. Introduction to Microelectronic Fabrication in the Addison-Wesley Modular Series on Solid State Devices, G.W. Neudeck and R.F. Pierret, eds. vol. 5, Addison-Wesley Publishing Co., Inc. (May 1993).

Jansen, H. et al. The Black Silicon Method IV: The Fabrication of Three-Dimensional Structures in Silicon with High Aspect Ratios for Scanning Probe Microscopy and Other Applications. MESA Res. Int, University of Twente, The Nethlerlands, (1995).

Laermer, F. et al. Bosch Deep Silicon Etching: Improving Uniformity and Etch Rate for Advanced MEMS Application. IEEE Catalog No. 99CH36291C, ISBN: 0-7803-5194-0 from the Twelfth IEEE International Conference on Micro Electro Mechanical Systems, Orlando FL, (Jan. 17-21, 1999).

Langer, R. Drug delivery and targeting. Nature 392 Supp, 5-10 (Apr. 30, 1998).

Lehmann, V. Porous Silicon—A New Material for MEMS. IEEE ISBN: 0-7803-2985-6/96 (1996).

Lin, L. et al. Silicon Processed Microneedles. The 7th International Conference on Solid-State Sensors and Actuators (1993).

Martin, C.R. et al. Template Synthesis of Organic Microtubules. J. Am. Chem. Soc. 112, 8976-8977 (1990).

(56) References Cited

OTHER PUBLICATIONS

Najafi, K. and Hetke, J.F. Strength Characterization of Silicon Microprobes in Neurophysiological Tissues. IEEE Transactions on Biomedical Engineering 37, 474-481 (May 1990).
Percutaneous Absorption, R.L. Bronaugh and H.I. Maibach, eds. Marcel Dekker, Inc., New York (1989).
Prausnitz, M.R. Reversible Skin Permeabilization for Transdermal Delivery of Macromolecules. Critical Reviews in Therapeutic Drug Carrier Systems 14, 455-483 (1997).
Quan, M. Plasma etch yields microneedle arrays. Electronic Eng. Times, p. 63 (Jul. 13, 1996).
Reiss, S.M. Glucose- and Blood-Monitoring Systems Vie for Top Spot. Biophotonics International p. 43-46 (May/Jun. 1997).
Runyan, W.R. and Bean, K.E. Semiconductor Integrated Circuit Processing Technology, Addison-Wesley Publishing Co. (1990).
Schift, H. et al. Fabrication of replicated high precision insert elements for micro-optical bench arrangements. SPIE vol. 3513, p. 122-134 from SPIE Conference on Microelectronic Structures and MEMS for Optical Processing IV, Santa Clara (Sep. 1998).
Single-crystal whiskers. Biophotonics Int'l, p. 64 (Nov./Dec. 1996).
Talbot, N.H. and Pisano, A.P. Polymolding: Two Wafer Polysilicon Micromolding of Closed-Flow Passages for Microneedles and Microfluidic Devices. Solid-State Sensor and Actuator Workshop, Hilton Head Island, SC (Jun. 8-11, 1998).
Transdermal Drug Delivery, J. Hadgraft and R.H. Guy, eds. Marcel Dekker, Inc., New York (1989).
Trimmer, W. et al. Injection of DNA into Plant and Animal Tissues with Micromechanical Piercing Structures. IEEE Catalog No. 95CH35754, ISBN: 0-7803-2503-6 from Micro Electro Mechanical Systems, Amsterdam p. 111-115 (1995).
Weber, L. et al. Micro molding—a powerful tool for the large scale production of precise microstructures. SPIE No. 0-8194-2277-0/96, vol. 2879, p. 156-167 (1996).
Zuska, P. Microtechnology Opens Doors to the Universe of Small Space. MD&DI (1997).

\* cited by examiner

GAS PRESSURE ACTUATED MICRONEEDLE ARRAYS, AND SYSTEMS AND METHODS RELATING TO SAME

REFERENCE TO RELATED APPLICATIONS

This application claims priority to U.S. Ser. No. 60/323,852 filed Sep. 21, 2001, entitled MICRONEEDLE SYSTEMS AND METHODS RELATING TO SAME, and naming Robert R. Gonnelli as inventor, the contents of which are hereby incorporated by reference.

TECHNICAL FIELD

The invention relates microneedle systems, microneedle arrays, and methods relating to same.

BACKGROUND

Microneedles can be used, for example, to sample analyte content of a subject (e.g., a human) and/or to delivery a medicament (e.g., a drug) to a subject (e.g., a human).

Topical delivery of drugs is a very useful method for achieving systemic or localized pharmacological effects. The main challenge in transcutaneous drug delivery is providing sufficient drug penetration across the skin. The skin consists of multiple layers starting with a stratum cornuem layer about (for humans) twenty (20) microns in thickness (comprising dead cells), a viable epidermal tissue layer about seventy (70) microns in thickness, and a dermal tissue layer about two (2) mm in thickness.

The thin layer of stratum corneum represents a major barrier for chemical penetration through skin. The stratum corneum is responsible for 50% to 90% of the skin barrier property, depending upon the drug material's water solubility and molecular weight. The epidermis comprises living tissue with a high concentration of water. This layer presents a lesser barrier for drug penetration. The dermis contains a rich capillary network close to the dermal/epidermal junction, and once a drug reaches the dermal depth it diffuses rapidly to deep tissue layers (such as hair follicles, muscles, and internal organs), or systemically via blood circulation.

Current topical drug delivery methods are based upon the use of penetration enhancing methods, which often cause skin irritation, and the use of occlusive patches that hydrate the stratum corneum to reduce its barrier properties. Only small fractions of topically applied drug penetrates through skin, with very poor efficiency.

Conventional methods of biological fluid sampling and non-oral drug delivery are normally invasive. That is, the skin is lanced in order to extract blood and measure various components when performing fluid sampling, or a drug delivery procedure is normally performed by injection, which causes pain and requires special medical training.

Alternatives to drug delivery by injection are known. One alternative is disclosed in U.S. Pat. No. 3,964,482 (by Gerstel), in which an array of either solid or hollow microneedles is used to penetrate through the stratum corneum, into the epidermal layer, but not to the dermal layer.

The use of microneedles has great advantages in that intracutaneous drug delivery can be accomplished without pain and without bleeding. Microneedles are sufficiently long to penetrate through the stratum corneum skin layer and into the epidermal layer, yet are also sufficiently short to not penetrate to the dermal layer. Of course, if the dead cells have been completely or mostly removed from a portion of skin, then a very minute length of microneedle could be used to reach the viable epidermal tissue Although microneedle technology shows much promise for drug delivery, it would be a further advantage if a microneedle apparatus could be provided that allows for the delivery of a drug into a patient with added ease.

SUMMARY

In general, the invention relates to microneedles, microneedle arrays, and systems and methods relating to same. Accordingly, it is a primary advantage of the invention to provide a microneedle array which can perform intracutaneous drug delivery. It is another advantage of the invention to provide a microneedle array that can deliver drug more easily into a patient. It is a further advantage of the invention to provide a microneedle array as part of a gas actuated system. It is a further advantage of the invention to provide a microneedle array as part of a closed-loop system to control drug delivery. It is a still further advantage of the system to provide a microneedle drug delivery system which delivers substantially all of the therapeutic agent contained in the device. It is a yet further advantage of the invention to provide a method for manufacturing an array of microneedles using microfabrication techniques, including known semiconductor fabrication techniques. It is still another advantage of the invention to provide a method of manufacturing an array of microneedles comprising a plastic material by a "self-molding" method, a micromolding method, a microembossing method, or a microinjection method.

In one aspect, the invention features a microneedle array and a gas source (e.g., an electrolytic cell). The gas source is configured so that, when the gas source forms a gas, a fluid between the microneedle array and the gas source passes through at least one of the microneedles in the microneedle array.

The system can further include a fluid reservoir between the microneedle array and the gas source. The fluid reservoir may contain a fluid, such as water or saline. The fluid reservoir can contain, for example, a therapeutic agent (e.g., a drug, such as insulin).

In certain embodiments, therapeutic agent may be selected from vaccines, chemotherapy agents, pain relief agents, dialysis-related agents, blood thinning agents, and compounds (e.g., monoclonal compounds) that can be targeted to carry compounds that can kill cancer cells. The therapeutic agent may also be selected from proteins, enzymes, polysaccharides, polynucleotide molecules, and synthetic organic and inorganic compounds. Representative agents include anti-infectives, hormones, growth regulators, drugs regulating cardiac action or blood flow, and drugs for pain control. The drug can be for local treatment or for regional or systemic therapy. The therapeutic agent may be selected from insulin, heparin, morphine, interferon, EPO, vaccines towards tumors, and vaccines towards infectious diseases. In a preferred embodiment, the therapeutic agent is insulin.

The system can further include a flexible layer (e.g., a membrane) between the gas source and the microneedle array. The fluid reservoir can be located between the flexible layer and the gas source.

The flexible layer may be resilient or elastic. The flexible layer may include slits, pores, or other such openings which are generally closed but open upon application of pressure, such as gas pressure from a gas source, to allow substances from the fluid reservoir to pass therethrough. The flexible layer may have openings that are blocked by one-way valves which open upon application of pressure, such as gas pressure from a gas source, to allow substances from the fluid reservoir to pass therethrough. The valves may be formed from a variety of materials that are compatible with the substance from the fluid reservoir. Preferred materials include natural and synthetic polymers, metals, plastics, rubbers, semiconductors, organics, composites and any other non-porous material.

The flexible layer can be semi-permeable. For example, the flexible layer can allow one or more desired substances (e.g., one or more desired therapeutic agents) to pass therethrough. As an additional example, the flexible layer can substantially prevent one or more undesired substances from passing therethrough. In some embodiments, both features can be provided by a flexible layer.

The flexible layer formed from a variety of materials that are compatible with the substance from the fluid reservoir. Preferred materials include natural and synthetic polymers, metals, plastics, rubbers, semiconductors, organics, composites, and any other appropriate material.

In another aspect, the invention features methods of making one of the microneedle arrays. The method can include, for example, one or more microfabrication steps.

In certain embodiments, microneedles, microneedle arrays, and/or microneedle systems can be involved in delivering drugs. For example, a system can include a sample section and a delivery section. The sections can be in communication so that the delivery section delivers one or more desired medicaments in response to a signal from the sample section. Optionally, a dose control system may be employed to select or regulate a delivered dose based, at least in part, on a change in an electrical, magnetic or optical parameter.

In a further aspect, the invention features methods of using such systems.

BRIEF DESCRIPTION OF THE DRAWINGS

The foregoing and other objects and advantages of the invention will be appreciated more fully from the following further description thereof, with reference to the accompanying drawings wherein.

DETAILED DESCRIPTION

Figure 1A:
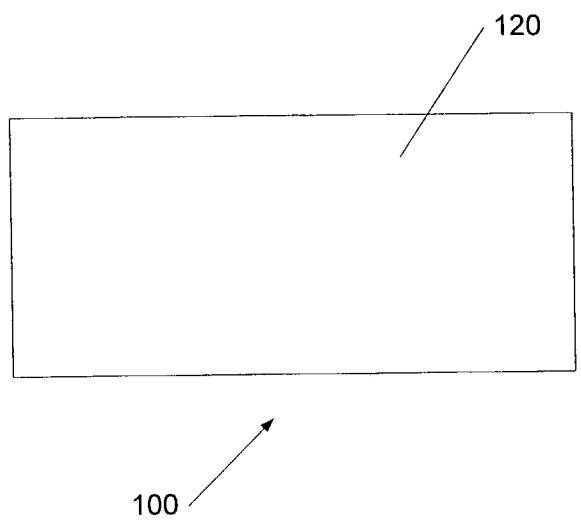
FIGS. 1A, 1B, and 1C are top, cross-sectional, and bottom views, respectively, of an embodiment of a microneedle system.

To provide an overall understanding of the invention, certain illustrative embodiments will now be described, including a microneedle, and microneedle system that detects the presence of a biological compound or concentration of a biological compound of interest. However, it will be understood by one of ordinary skill in the art that the systems and methods described herein can be adapted and modified for other suitable applications and that such other additions and modifications will not depart from the scope hereof.

The devices disclosed herein are useful in transport of material into or across biological barriers including the skin (or parts thereof); the blood-brain barrier; mucosal tissue (e.g., oral, nasal, ocular, vaginal, urethral, gastrointestinal, respiratory); blood vessels; lymphatic vessels; or cell membranes (e.g., for the introduction of material into the interior of a cell or cells). The biological barriers can be in humans or other types of animals, as well as in plants, insects, or other organisms, including bacteria, yeast, fungi, and embryos.

The microneedle devices can be applied to tissue internally with the aid of a catheter or laparoscope. For certain applications, such as for drug delivery to an internal tissue, the devices can be surgically implanted.

The microneedle device disclosed herein is typically applied to skin. The stratum corneum is the outer layer, generally between 10 and 50 cells, or between 10 and 20 µm thick. Unlike other tissue in the body, the stratum corneum contains "cells" (called keratinocytes) filled with bundles of cross-linked keratin and keratohyalin surrounded by an extracellular matrix of lipids. It is this structure that is believed to give skin its barrier properties, which prevents therapeutic transdermal administration of many drugs. Below the stratum corneum is the viable epidermis, which is between 50 and 100 µm thick. The viable epidermis contains no blood vessels, and it exchanges metabolites by diffusion to and from the dermis. Beneath the viable epidermis is the dermis, which is between 1 and 3 mm thick and contains blood vessels, lymphatics, and nerves.

The microneedle devices disclosed herein in some embodiments include a substrate; one or more microneedles; a reservoir for delivery of drugs; a gas source, and, optionally, pump(s), sensor(s), and/or microprocessor(s) to control the interaction of the foregoing.

The substrate of the device can be constructed from a variety of materials, including metals, ceramics, semiconductors, organics, polymers, and composites. The substrate includes the base to which the microneedles are attached or integrally formed. A reservoir may also be attached to the substrate.

The microneedles of the device can be constructed from a variety of materials, including metals, ceramics, semiconductors, organics, polymers, and composites. Preferred materials of construction include pharmaceutical grade stainless steel, gold, titanium, nickel, iron, gold, tin, chromium, copper, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluorethylene and polyesters.

Generally, the microneedles should have the mechanical strength to remain intact for delivery of drugs, and to serve as a conduit for the collection of biological fluid and/or tissue, while being inserted into the skin, while remaining in place for up to a number of days, and while being removed. In certain embodiments, the microneedles may be formed of biodegradable polymers. However, for these embodiments that employ biodegratable materials, the mechanical requirement may be less stringent.

The microneedles can be formed of a porous solid, with or without a sealed coating or exterior portion, or hollow. As used herein, the term "porous" means having pores or voids throughout at least a portion of the microneedle structure, sufficiently large and sufficiently interconnected to permit passage of fluid and/or solid materials through the microneedle. As used herein, the term "hollow" means having one or more substantially annular bores or channels through the interior of the microneedle structure, having a diameter sufficiently large to permit passage of fluid and/or solid materials through the microneedle. The annular bores may extend throughout all or a portion of the needle in the direction of the tip to the base, extending parallel to the direction of the needle or branching or exiting at a side of the needle, as appropriate. A solid or porous microneedle can be hollow. One of skill in the art can select the appropriate porosity and/or bore features required for specific applications. For example, one can adjust the pore size or bore diameter to permit passage of the particular material to be transported through the microneedle device.

The microneedles can have straight or tapered shafts. A hollow microneedle that has a substantially uniform diameter, which needle does not taper to a point, is referred to herein as a "microtube." As used herein, the term "microneedle" includes, although is not limited to both microtubes and tapered needles unless otherwise indicated. In a preferred embodiment, the diameter of the microneedle is greatest at the base end of the microneedle and tapers to a point at the end distal the base. The microneedle can also be fabricated to have a shaft that includes both a straight (untapered) portion and a tapered portion.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The shaft can have one or more bores. The cross-sectional dimensions typically are between about 10 nm and 1 mm, preferably between 1 micron and 200 microns, and more preferably between 10 and 100 µm. The outer diameter is typically between about 10 µm and about 100 µm, and the inner diameter is typically between about 3 µm and about 80 µm.

The length of the microneedles typically is between about 1 and 1 mm, preferably between 10 microns and 500 microns, and more preferably between 30 and 200 µm. The length is selected for the particular application, accounting for both an inserted and uninserted portion. An array of microncedles can include a mixture of microneedles having, for example, various lengths, outer diameters, inner diameters, cross-sectional shapes, and spacings between the microneedles.

The microneedles can be oriented perpendicular or at an angle to the substrate. Preferably, the microneedles are oriented perpendicular to the substrate so that a larger density of microneedles per unit area of substrate can be provided. An array of microneedles can include a mixture of microneedle orientations, heights, or other parameters.

In a preferred embodiment of the device, the substrate and/or microneedles, as well as other components, are formed from flexible materials to allow the device to fit the contours of the biological barrier, such as the skin, vessel walls, or the eye, to which the device is applied. A flexible device will facilitate more consistent penetration during use, since penetration can be limited by deviations in the attachment surface. For example, the surface of human skin is not flat due to dermatoglyphics (i.e. tiny wrinkles) and hair.

The microneedle device may include a reservoir that may or may not be, depending upon the embodiment, in communication with the microneedles. The reservoir can be attached to the substrate by any suitable means. In a preferred embodiment, the reservoir is attached to the back of the substrate (opposite the microneedles) around the periphery, using an adhesive agent (e.g., glue). A gasket may also be used to facilitate formation of a fluid-tight seal.

In one embodiment, the reservoir contains drug, for delivery through the microneedles. The reservoir may be a hollow vessel, a porous matrix, or a solid form including drug which is transported therefrom. The reservoir can be formed from a variety of materials that are compatible with the drug or biological fluid contained therein. Preferred materials include natural and synthetic polymers, metals, ceramics, semiconductors, organics, and composites.

The microneedle device can include one or a plurality of chambers for storing materials to be delivered. In the embodiment having multiple chambers, each can be in fluid connection with all or a portion of the microneedles of the device array. In one embodiment, at least two chambers are used to separately contain drug (e.g., a lyophilized drug, such as a vaccine) and an administration vehicle (e.g., saline) in order to prevent or minimize degradation during storage. Immediately before use, the contents of the chambers are mixed. Mixing can be triggered by any means, including, for example, mechanical disruption (i.e. puncturing or breaking), changing the porosity, or electrochemical degradation of the walls or membranes separating the chambers. In another embodiment, a single device is used to deliver different drugs, which are stored separately in different chambers. In this embodiment, the rate of delivery of each drug can be independently controlled.

In one embodiment, the reservoir is in direct contact with the microneedles and have holes through which drug could exit the reservoir and flow into the interior of hollow or porous microneedles. In another embodiment, the reservoir has holes which permit the drug to transport out of the reservoir and onto the skin surface. From there, drug is transported into the skin, either through hollow or porous microneedles, along the sides of solid microneedles, or through pathways created by microneedles in the skin.

The microneedle device may also be capable of transporting material across the barrier at a useful rate. For example, the microneedle device must be capable of delivering drug across the skin at a rate sufficient to be therapeutically useful. The device may include a housing with microelectronics and other micromachined structures to control the rate of delivery either according to a preprogrammed schedule or through active interface with the patient, a healthcare professional, or a biosensor. The rate can be controlled by manipulating a variety of factors, including the characteristics of the drug formulation to be delivered (e.g., its viscosity, electric charge, and chemical composition); the dimensions of each microneedle (e.g., its outer diameter and the area of porous or hollow openings); the number of microneedles in the device; the application of a driving force (e.g., a concentration gradient, a voltage gradient, a pressure gradient); and the use of a valve.

The rate also can be controlled by interposing between the drug in the reservoir and the opening(s) at the base end of the microneedle polymeric or other materials selected for their diffusion characteristics. For example, the material composition and layer thickness can be manipulated using methods known in the art to vary the rate of diffusion of the drug of interest through the material, thereby controlling the rate at which the drug flows from the reservoir through the microneedle and into the tissue.

Transportation of molecules through the microneedles can be controlled or monitored using, for example, various combinations of valves, pumps, sensors, actuators, and microprocessors. These components can be produced using standard manufacturing or microfabrication techniques. Actuators that may be useful with the microneedle devices disclosed herein include micropumps, microvalves, and positioners. In a preferred embodiment, a microprocessor is programmed to control a pump or valve, thereby controlling the rate of delivery.

Flow of molecules through the microneedles can occur based on diffusion, capillary action, or can be induced using conventional mechanical pumps or nonmechanical driving forces, such as electroosmosis or electrophoresis, or convection. For example, in electroosmosis, electrodes are positioned on the biological barrier surface, one or more microneedles, and/or the substrate adjacent the needles, to create a convective flow which carries oppositely charged ionic species and/or neutral molecules toward or into the biological barrier. In a preferred embodiment, the microneedle device is used in combination with another mechanism that enhances the permeability of the biological barrier, for example by increasing cell uptake or membrane disruption, using electric fields, ultrasound, chemical enhancers, viruses, pH, heat and/or light.

Passage of the microneedles, or drug to be transported via the microneedles, can be manipulated by shaping the microneedle surface, or by selection of the material forming the microneedle surface (which could be a coating rather than the microneedle per se). For example, one or more grooves on the outside surface of the microneedles can be used to direct the passage of drug, particularly in a liquid state. Alternatively, the physical surface properties of the microneedle could be manipulated to either promote or inhibit transport of material along the microneedle surface, such as by controlling hydrophilicity or hydrophobicity.

The flow of molecules can be regulated using a wide range of valves or gates. These valves can be the type that are selectively and repeatedly opened and closed, or they can be single-use types. For example, in a disposable, single-use drug delivery device, a fracturable barrier or one-way gate may be installed in the device between the reservoir and the opening of the microneedles. When ready to use, the barrier can be broken or gate opened to permit flow through the microneedles. Other valves or gates used in the microneedle devices can be activated thermally, electrochemically, mechanically, or magnetically to selectively initiate, modulate, or stop the flow of molecules through the needles. In a preferred embodiment, flow is controlled by using a rate-limiting membrane as a "valve."

The microneedle devices can further include a flowmeter or other dose control system to monitor flow and optionally control flow through the microneedles and to coordinate use of the pumps and valves.

Useful sensors may include sensors of pressure, temperature, chemicals, and/or electromagnetic fields. Biosensors can be employed, and in one arrangement, are located on the microneedle surface, inside a hollow or porous microneedle, or inside a device in communication with the body tissue via the microneedle (solid, hollow, or porous). These microneedle biosensors may include any suitable transducers, including but not limited to potentiometric, amperometric, optical, magnetic and physiochemical. An amperometric sensor monitors currents generated when electrons are exchanged between a biological system and an electrode. Blood glucose sensors frequently are of this type. As described herein, the sensors may be formed to sense changes resulting from an election transfer agent interacting with analyte or analytes of interest.

The microneedle may function as a conduit for fluids, solutes, electric charge, light, or other materials. In one embodiment, hollow microneedles can be filled with a substance, such as a gel, that has a sensing functionality associated with it. In an application for sensing based on binding to a substrate or reaction mediated by an enzyme, the substrate or enzyme can be immobilized in the needle interior, which would be especially useful in a porous needle to create an integral needle/sensor.

Wave guides can be incorporated into the microneedle device to direct light to a specific location, or for dection, for example, using means such as a pH dye for color evaluation. Similarly, heat, electricity, light or other energy forms may be precisely transmitted to directly stimulate, damage, or heal a specific tissue or intermediary (e.g., tattoo remove for dark skinned persons), or diagnostic purposes, such as measurement of blood glucose based on IR spectra or by chromatographic means, measuring a color change in the presence of immobilized glucose oxidase in combination with an appropriate substrate.

A collar or flange also can be provided with the device, for example, around the periphery of the substrate or the base. It preferably is attached to the device, but alternatively can be formed as integral part of the substrate, for example by forming microneedles only near the center of an "oversized" substrate. The collar can also emanate from other parts of the device. The collar can provide an interface to attach the microneedle array to the rest of the device, and can facilitate handling of the smaller devices.

In a preferred embodiment, the microneedle device includes an adhesive to temporarily secure the device to the surface of the biological barrier. The adhesive can be essentially anywhere on the device to facilitate contact with the biological barrier. For example, the adhesive can be on the surface of the collar (same side as microneedles), on the surface of the substrate between the microneedles (near the base of the microneedles), or a combination thereof.

Figure 1B:
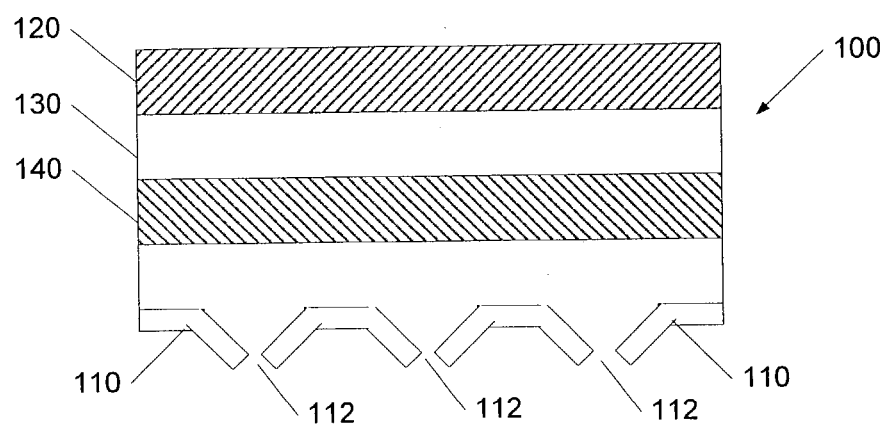
Figure 1C:
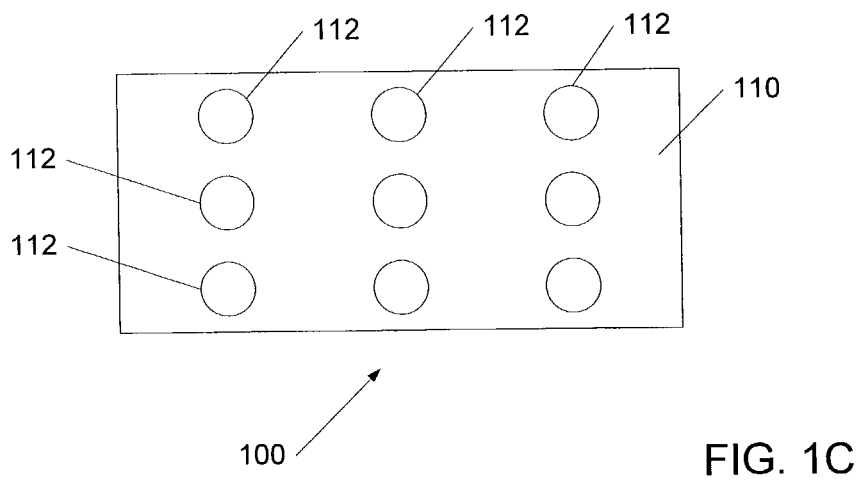

FIGS. 1A-C show an embodiment of a microneedle system 100 that includes a microneedle array 110, a gas source (e.g., an electrolytic cell) 120, a fluid reservoir 130, and a flexible layer (e.g., a membrane) 140. During use, gas source 120 produces a gas (e.g., oxygen) that forces a fluid contained in reservoir 130 through flexible layer 140 and through microneedles 112 of array 110.

FIG. 1B depicts microneedles 112 that are generally between about 1 µm and 1 mm in length. The diameter and length of microneedles 112 both affect pain as well as functional properties of the needles. In transdermal applications, the "insertion depth" of a microneedle is preferably less than about 200 µm, more preferably about 30 µm, so that insertion of the microneedles into the skin through the stratum corneum does not penetrate past the epidermis into the dermis, thereby avoiding contacting nerves and reducing the potential for causing pain. In such applications, the actual length of the microneedles may be longer, since the portion of the microneedles distal the tip may not be inserted into the skin; the uninserted length depends on the particular device design and configuration. The actual (overall) height or length of microneedles should be equal to the insertion depth plus the uninserted length. In applications where the microneedles 112 are employed to sample blood or tissue, the length of the microneedle is selected to allow sufficient penetration for blood to flow into the microneedle or the desired tissue be penetrated.

In certain embodiments, flexible layer 140 is formed of a flexible material that are compatible with the substances from fluid reservoir 130 rubber, a polymer, a plastic, a metal, or any other material with the appropriate characteristics. Preferred materials include natural and synthetic polymers, metals, plastics, rubbers, semiconductors, organics, composites, and any other appropriate material.

Reservoir 130 generally contains a fluid, such as a therapeutic agent (e.g., a drug). Therapeutic agents include, for example, vaccines, chemotherapy agents, pain relief agents, dialysis-related agents, blood thinning agents, and compounds (e.g., monoclonal compounds) that can be targeted to carry compounds that can kill cancer cells. Examples of therapeutic agents include, insulin, heparin, morphine, interferon, EPO, vaccines towards tumors, and vaccines towards infectious diseases.

Flexible layer 140 is generally formed of a material having sufficient flexibility to move when a gas is produced by gas source 120. In certain embodiments, flexible layer 140 is formed of a material that is partially porous. Deformation that allows for fluid to pass may be plastic or elastic, depending upon the material employed. Materials and methods of manufacture appropriate for flexible layer 140 are known to those skilled in the art.

Figure 2A:
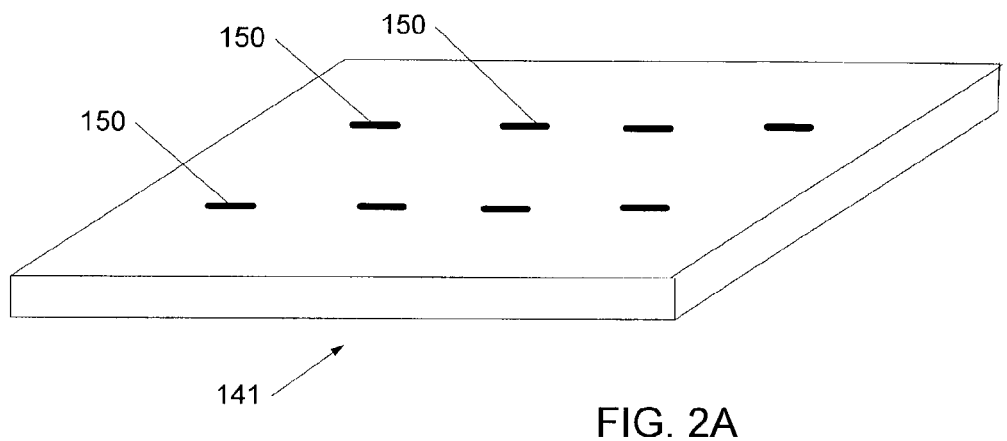
FIGS. 2A, 2B, and 2C are a top and two cross-sectional views, respectively, of three embodiments of a flexible layer, such as flexible layer 140.
Figure 2B:
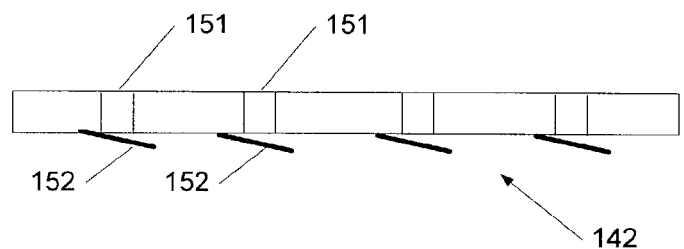
Figure 2C:
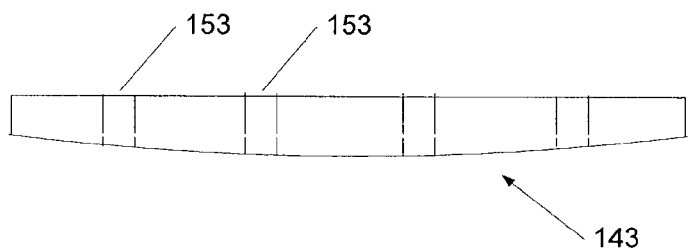

FIGS. 2A, 2B, and 2C depict three different embodiments of a flexible layer that may be employed in the device of the present invention. FIG. 2A shows a top view of an embodiment of flexible layer 141 which includes slits 150. Flexible layer 141 may be made from a resilient, elastic material such that slits 150 only allow substances to flow therethrough when pressure, such as gas pressure from a gas source, is applied. If pressure is removed, slits 150 are effectively closed and do not allow any substances to pass therethrough.

FIG. 2B shows a cross-sectional view of an embodiment of flexible layer 142 including pores 151 extending through flexible layer 142 and one-way valves 152. One-way valves 152 are positioned such that they extend away from the end of pores 151, i.e., open, when pressure, such as gas pressure from a gas source, is applied from the opposite side of flexible layer 142. When pressure is applied, one-way valves 152 open, thus allowing substances in the fluid reservoir to flow through flexible layer 142. Flexible layer 142 may be made from a resilient, non-porous material such that one-way valves 152 only allow substances to flow therethrough when pressure, such as gas pressure from a gas source, is applied. If pressure is removed, one-way valves 152 are closed and do not allow any substances to pass therethrough.

FIG. 2C shows a cross-sectional view of an embodiment of flexible layer 143 including pores 153 extending through flexible layer 143. Pores 153 may be filled with a material, such as a salt, a polymer, etc., that dissolves upon a change catalyzed by the addition of gas from a gas source to the fluid reservoir. This change may be a change in the pH, e.g., the acidity or basicity, of the contents of the fluid reservoir. Upon addition of the gas, the contents of the fluid reservoir dissolve, thus allowing substances in the fluid reservoir to flow through flexible layer 143. Flexible layer 143 may be made from a resilient, non-porous material such that pores 153 only allow substances to flow therethrough when gas is added and causes a change in the contents of the fluid reservoir, such as pH.

In certain embodiments, microneedles, microneedle arrays, and/or microneedle systems can be involved in delivering drugs. For example, a system can include a sample section and a delivery section. The sections can be in communication so that the delivery section delivers one or more desired medicaments in response to a signal from the sample section.

As discussed above, FIG. 1B shows a cross-sectional view of a schematic of a preferred embodiment of the microneedle device 100 in a transdermal application. The device 100 is applied to the skin such that the microneedles 112 penetrate through the stratum corneum and enter the viable epidermis so that the tip of the microneedle at least penetrates into the viable epidermis. In a preferred embodiment, drug molecules in fluid reservoir 130 flow through or around the microneedles and into the viable epidermis, where the drug molecules then diffuse into the dermis for local treatment or for transport through the body.

In embodiments, microneedles, microneedle arrays, and/or microneedle systems can be involved in delivering drugs. For example, a system can include a sample section and a delivery section. The sections can be in communication so that the delivery section delivers one or more desired medicaments in response to a signal from the sample section.

The device may be used for single or multiple uses for rapid transport across a biological barrier or may be left in place for longer times (e.g., hours or days) for long-term transport of molecules. Depending on the dimensions of the device, the application site, and the route in which the device is introduced into (or onto) the biological barrier, the device may be used to introduce or remove molecules at specific locations.

Materials and methods of manufacturing as well as various design features and methods of using, the microneedles and microneedle arrays described herein are disclosed, for example, in Published PCT patent application WO 99/64580, entitled "Microneedle Devices and Methods of Manufacture and Use Thereof," Published PCT patent application WO 00/74763, entitled "Devices and Methods for Enhanced Microneedle Penetration or Biological Barriers," Published PCT patent application WO 01/49346, entitled "Stacked Microneedle Systems," and commonly owned U.S. Provisional Patent Application Ser. No. 60/323,417, filed on Sep. 19, 2001, and entitled "Microneedles, Microneedle Arrays, and Systems and Methods Relating to Same," each of which is hereby incorporated by reference.

Materials, methods of manufacture, and embodiments of gas source 120 are disclosed, for example, in U.S. Pat. Nos. 4,402,817, 4,522,698, 4,902,278, 4,687,423, commonly owned U.S. Provisional Patent Application No. 60/250,538, entitled "Fluid Delivery Systems," commonly owned U.S. Provisional Patent Application No. 60/250,295, entitled "Sensor System," commonly owned U.S. Provisional Patent Application No. 60/250,409, entitled "Electrochemical Cell," commonly owned U.S. Provisional Patent Application No. 60/250,927, entitled "Fluid Delivery Systems and Methods," commonly owned U.S. Provisional Patent Application No. 60/250,408, entitled "Fluid Delivery Systems," commonly owned U.S. Provisional Patent Application No. 60/250,403, entitled "Fluid Delivery Device," commonly owned U.S. Provisional Patent Application No. 60/250,422, entitled "Fluid Delivery Systems and Methods," commonly owned U.S. Provisional Patent Application No. 60/250,410, entitled "Injection Devices," each of which is hereby incorporated by reference.

To control the transport of material out of or into the device through the microneedles, a variety of forces or mechanisms can be employed. These include pressure gradients, concentration gradients, electricity, ultrasound, receptor binding, heat, chemicals, and chemical reactions. Mechanical or other gates in conjunction with the forces and mechanisms described above can be used to selectively control transport of the material.

In particular embodiments, the device should be "user-friendly." For example, in some transdermal applications, affixing the device to the skin should be relatively simple, and not require special skills. This embodiment of a microneedle may include an array of microneedles attached to a housing containing drug in an internal reservoir, wherein the housing has a bioadhesive coating around the microneedles. The patient can remove a peel-away backing to expose an adhesive coating, and then press the device onto a clean part of the skin, leaving it to administer drug over the course of, for example, several days.

The device may be attached to the patient by a belt, strap, or adhesive (e.g., it can be attached to the patient's skin by an adhesive patch). In some instances, an adhesive and a second security device (e.g., a belt or strap) can be used.

Essentially any drug or other bioactive agents can be delivered using these devices. Drugs can be proteins, enzymes, polysaccharides, polynucleotide molecules, and synthetic organic and inorganic compounds. A preferred drug is insulin. Representative agents include anti-infectives, hormones, growth regulators, drugs regulating cardiac action or blood flow, and drugs for pain control. The drug can be for local treatment or for regional or systemic therapy. The following are representative examples, and disorders they are used to treat: Calcitonin, osteoporosis; Enoxaprin, anticoagulant; Etanercept, rheumatoid arthritis; Erythropoietin, anemia; Fentanyl, postoperative and chronic pain; Filgrastin, low white blood cells from chemotherapy; Heparin, anticoagulant; Insulin, human, diabetes; Interferon Beta I a, multiple sclerosis; Lidocaine, local anesthesia; Somatropin, growth hormone; Sumatriptan, and migraine headaches.

In this way, many drugs can be delivered at a variety of therapeutic rates. The rate can be controlled by varying a number of design factors, including the rate at which the gas expands the outer diameter of the microneedle, the number and size of pores or channels in each microneedle, the number of microneedles in an array, the magnitude and frequency of application of the force driving the drug through the microneedle and/or the holes created by the microneedles. For example, devices designed to deliver drug at different rates might have more microneedles for more rapid delivery and fewer microneedles for less rapid delivery. As another example, a device designed to deliver drug at a variable rate could vary the driving force (e.g., pressure gradient controlled by a pump) for transport according to a schedule which was pre-programmed or controlled by, for example, the user or his doctor. The devices can be affixed to the skin or other tissue to deliver drugs continuously or intermittently, for durations ranging from a few seconds to several hours or days.

One of skill in the art can measure the rate of drug delivery for particular microneedle devices using in vitro and in vivo methods known in the art. For example, to measure the rate of transdermal drug delivery, human cadaver skin mounted on standard diffusion chambers can be used to predict actual rates. See Hadgraft & Guy, eds., Transdermal Drug Delivery: Developmental Issues and Research Initiatives (Marcel Dekker, New York 1989); Bronaugh & Maibach, Percutaneous Absorption, Mechanisms-Methodology—Drug Delivery (Marcel Dekker, New York 1989). After filling the compartment on the dermis side of the diffusion chamber with saline, a microneedle array is inserted into the stratum corneum; a drug solution is placed in the reservoir of the microneedle device; and samples of the saline solution are taken over time and assayed to determine the rates of drug transport.

In an alternate embodiment, biodegradable or non-biodegradable microneedles can be used as the entire drug delivery device, where biodegradable microneedles are a preferred embodiment. For example, the microneedles may be formed of a biodegradable polymer containing a dispersion of an active agent for local or systemic delivery. The agent could be released over time, according to a profile determined by the composition and geometry of the microneedles, the concentration of the drug and other factors. In this way, the drug reservoir is within the matrix of one or more of the microneedles.

In another alternate embodiment, these microneedles may be purposefully sheared off from the substrate after penetrating the biological barrier. In this way, a portion of the microneedles would remain within or on the other side of the biological barrier and a portion of the microneedles and their substrate would be removed from the biological barrier. In the case of skin, this could involve inserting an array into the skin, manually or otherwise breaking off the microneedles tips and then remove the base of the microneedles. The portion of the microneedles which remains in the skin or in or across another biological barrier could then release drug over time according to a profile determined by the composition and geometry of the microneedles, the concentration of the drug and other factors. In a preferred embodiment, the microneedles are made of a biodegradable polymer. The release of drug from the biodegradable microneedle tips could be controlled by the rate of polymer degradation. Microneedle tips could release drugs for local or systemic effect, but could also release other agents, such as perfume, insect repellent and sun block.

Microneedle shape and content could be designed to control the breakage of microneedles. For example, a notch could be introduced into microneedles either at the time of fabrication or as a subsequent step. In this way, microneedles would preferentially break at the site of the notch. Moreover, the size and shape of the portion of microneedles which break off could be controlled not only for specific drug release patterns, but also for specific interactions with cells in the body. For example, objects of a few microns in size are known to be taken up by macrophages. The portions of microneedles that break off could be controlled to be bigger or smaller than that to prevent uptake by macrophages or could be that size to promote uptake by macrophages, which could be desirable for delivery of vaccines.

In an alternate embodiment, microneedles may be purposefully sheared off from the substrate after penetrating the biological barrier, as described above. The portion of the microneedles which remain within or on the other side of the biological barrier could contain one or more biosensors. For example, the sensor could change color as its output. For microneedles sheared off in the skin, this color change could be observed through the skin by visual inspection or with the aid of an optical apparatus.

Other than transport of drugs and biological molecules, the microneedles may be used to transmit or transfer other materials and energy forms, such as light, electricity, heat, or pressure. The microneedles, for example, could be used to direct light to specific locations within the body, in order that the light can directly act on a tissue or on an intermediary, such as light-sensitive molecules in photodynamic therapy. The microneedles can also be used for aerosolization or delivery for example directly to a mucosal surface in the nasal or buccal regions or to the pulmonary system.

The microneedle devices disclosed herein also should be useful for controlling transport across tissues other than skin. For example, microneedles could be inserted into the eye across, for example, conjunctiva, sclera, and/or cornea, to facilitate delivery of drugs into the eye. Similarly, microneedles inserted into the eye could facilitate transport of fluid out of the eye, which may be of benefit for treatment of glaucoma. Microneedles may also be inserted into the buccal (oral), nasal, vaginal, or other accessible mucosa to facilitate transport into, out of, or across those tissues. For example, a drug may be delivered across the buccal mucosa for local treatment in the mouth or for systemic uptake and delivery. As another example, microneedle devices may be used internally within the body on, for example, the lining of the gastrointestinal tract to facilitate uptake of orally-ingested drugs or the lining of blood vessels to facilitate penetration of drugs into the vessel wall. For example, cardiovascular applications include using microneedle devices to facilitate vessel distension or immobilization, similarly to a stent, wherein the microneedles/substrate can function as a "staple-like" device to penetrate into different tissue segments and hold their relative positions for a period of time to permit tissue regeneration. This application would be particularly useful with biodegradable devices. These uses may involve invasive procedures to introduce the microneedle devices into the body or could involve swallowing, inhaling, injecting or otherwise introducing the devices in a non-invasive or minimally-invasive manner.

Those skilled in the art will know or be able to ascertain using no more than routine experimentation, many equivalents to the embodiments and practices described herein.

Accordingly, it will be understood that the invention is not to be limited to the embodiments disclosed herein, but is to be understood from the following claims, which are to be interpreted as broadly as allowed under the law.

I claim:

1. A microneedle device, comprising:
   a substrate,
   a microneedle array attached to or integrally formed on a base of the substrate,
   a fluid reservoir,
   a gas source, and
   a flexible layer which allows one or more substances from the fluid reservoir and gas from the gas source to pass therethrough,
   wherein said fluid reservoir is disposed between said gas source and said flexible layer and wherein activation of the gas source causes gas to flow into the fluid reservoir and forces a substance from the fluid reservoir, through the flexible layer, and through the microneedles of the microneedle array.

2. The device of claim 1, wherein the fluid reservoir contains a fluid.

3. The device of claim 2, wherein the fluid includes a therapeutic agent.

4. The device of claim 3, wherein the therapeutic agent is selected from vaccines, chemotherapy agents, pain relief agents, dialysis-related agents, blood thinning agents, and compounds that can be targeted to carry compounds that can kill cancer cells.

5. The device of claim 3, wherein the therapeutic agent is selected from proteins, enzymes, polysaccharides, polynucleotide molecules, and synthetic organic and inorganic compounds.

6. The device of claim 3, wherein the therapeutic agent is selected from anti-infectives, hormones, growth regulators, drugs regulating cardiac action or blood flow, and drugs for pain control.

7. The device of claim 3, wherein the therapeutic agent is selected from insulin, heparin, morphine, interferon, EPO, tumor vaccines, and infectious disease vaccines.

8. The device of claim 3, wherein the therapeutic agent is insulin.

9. The device of claim 1, wherein the flexible layer is resilient or elastic.

10. The device of claim 1, wherein the flexible layer has slits.

11. The device of claim 1, wherein the flexible layer has one-way valves.

12. The device of claim 1, wherein the flexible layer is semi-permeable.

13. The device of claim 1, wherein the flexible layer substantially prevents one or more substances from passing therethrough.

14. The device of claim 1, wherein the flexible layer is a material selected from the group consisting of a rubber, a polymer, a plastic, a metal, and a composite.

15. The device of claim 1, wherein the device is skin patch.

16. The device of claim 1, further comprising a chamber disposed between said flexible layer and said substrate.

17. A method for delivering a drug through a microneedle device, comprising
   providing a substrate,
   providing a microneedle array attached to or integrally formed on a base of the substrate,
   providing a gas source,
   providing a fluid reservoir comprising drug to be delivered,
   providing a flexible layer which allows drug from the fluid reservoir and gas from the gas source to pass therethrough, wherein the reservoir is disposed between the gas source and the flexible layer, and wherein activation of the gas source causes gas to flow into the fluid reservoir and forces drug from the fluid reservoir, through the flexible layer, and through the microneedle array, and
   activating the gas source to deliver drug.

18. The method of claim 17, further comprising providing a chamber disposed between said flexible layer and said substrate.

19. The device of claim 1, wherein the microneedle array comprises hollow microneedles.

20. The device of claim 1, wherein the microneedle array comprises porous microneedles.

21. The method of claim 17, wherein the microneedle array comprises hollow microneedles.

22. The method of claim 17, wherein the microneedle array comprises porous microneedles.

* * * * *